US008663647B2

(12) United States Patent
Tahara et al.

(10) Patent No.: US 8,663,647 B2
(45) Date of Patent: Mar. 4, 2014

(54) EPITOPE PEPTIDES DERIVED FROM VASCULAR ENDOTHELIAL GROWTH FACTOR RECEPTOR 1 AND VACCINES CONTAINING THESE PEPTIDES

(75) Inventors: Hideaki Tahara, Tokyo (JP); Takuya Tsunoda, Tokyo (JP); Masabumi Shibuya, Tokyo (JP); Shuichi Nakatsuru, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 13/566,933

(22) Filed: Aug. 3, 2012

(65) Prior Publication Data

US 2012/0294877 A1 Nov. 22, 2012

Related U.S. Application Data

(62) Division of application No. 13/040,177, filed on Mar. 3, 2011, now Pat. No. 8,257,711, which is a division of application No. 11/816,893, filed as application No. PCT/JP2006/303352 on Feb. 17, 2006, now Pat. No. 7,919,099.

(60) Provisional application No. 60/657,527, filed on Feb. 28, 2005.

(51) Int. Cl.
*A61K 39/08* (2006.01)

(52) U.S. Cl.
USPC ........................................ 424/185.1; 514/21.6

(58) Field of Classification Search
None
See application file for complete search history.

(56) References Cited

U.S. PATENT DOCUMENTS

| 5,712,380 | A | 1/1998 | Kendall et al. |
| 6,200,954 | B1 | 3/2001 | Ge et al. |
| 6,383,486 | B1 | 5/2002 | Davis-Smyth et al. |
| 7,514,084 | B2 | 4/2009 | Tahara et al. |
| 7,556,809 | B2 * | 7/2009 | Romero et al. ............ 424/185.1 |
| 2003/0157101 | A1 * | 8/2003 | Gambacorti-Passerini et al. ............ 424/144.1 |
| 2005/0130899 | A1 | 6/2005 | Itoh |
| 2005/0175624 | A1 | 8/2005 | Romero et al. |
| 2006/0216301 | A1 | 9/2006 | Tahara et al. |
| 2012/0156233 | A1 | 6/2012 | Tsujikawa et al. |

FOREIGN PATENT DOCUMENTS

| EP | 1 548 032 A1 | 6/2005 |
| JP | 2003/050140 A1 | 6/2003 |
| JP | 2004/018667 A1 | 3/2004 |
| JP | 2006/501145 A | 1/2006 |
| WO | WO 02/072627 A2 | 9/2002 |
| WO | WO02072627 | * 9/2002 |
| WO | WO 03/042243 A2 | 5/2003 |
| WO | 03/050140 A1 | 6/2003 |
| WO | WO 03/086450 A1 | 10/2003 |
| WO | WO03086450 | * 10/2003 |
| WO | 2004/018667 | 3/2004 |
| WO | WO 2004/024766 A1 | 3/2004 |
| WO | WO 2004024766 | * 3/2004 |

OTHER PUBLICATIONS

Baxevanis, C. N, et al., "Immunogenic HER-2/neu peptides as tumor vaccines," *Cancer Immunol Immunother*, 2006, vol. 55, No. 1, pp. 85-95. Epub Oct. 27, 2005.

Dionne, et al., "Functional characterization of CTL against gp100 altered peptide ligands," *Cancer Immunol Immunother*., vol. 52(4), pp. 199-206 (Apr. 2003, Epub Feb. 18, 2003).

Dionne, et al., "Her-2/neu altered peptide ligand-induced CTL responses: implications for peptides with increased HLA affinity and T-cell-receptor interaction," *Cancer Immunol Immunother*., vol. 53(4), pp. 307-314 (Apr. 2004, Epub Nov. 5, 2003).

Falk, et al., "Allele-specific motifs revealed by sequencing of self-peptides eluted from MHC molecules," *Nature*, vol. 351(6324), pp. 290-296 (May 23, 1991).

Ferrara, N. et al., "The Biology of Vascular Endothelial Growth Factor," *Endocrine Reviews*, 1997, vol. 18, No. 1, pp. 4-25.

Hoffman, et al. "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).

Kondo et al.; "Prominent roles of secondary anchor residues in peptide binding to HLA-A24 human class 1 molecules"; 1995; *J. Immunol.*; vol. 155, No. 9, pp. 4307-4312.

Kubo et al.; "Definition of specific peptide motifs for four major HLA-A alleles"; 1994; *J. Immunol.*; vol. 152, No. 8, pp. 3913-3924.

Leggatt, G. R, et al., "The Importance of Pairwise Interactions Between Peptide Residues in the Delineation of TCR Specificity," *J Immunol*, 1998, vol. 161, No. 9, pp. 4728-4735.

Mestas, J, et al., "Of Mice and Not Men: Differences between Mouse and Human Immunology," *J Immunol*, 2004, vol. 172, No. 5, pp. 2731-2738.

(Continued)

*Primary Examiner* — Phuong Huynh
(74) *Attorney, Agent, or Firm* — Kilpatrick Townsend & Stockton LLP

(57) ABSTRACT

The present invention provides immunogenic peptides comprising the amino acid sequence of SEQ ID NO: 1, 2, 13, 32, and peptides comprising the above-mentioned amino acid sequences in which 1, 2, or several amino acids are substituted or added, and having cytotoxic T cell inducibility, and also provides drugs for treating or preventing tumors comprising these peptides. The peptides of this invention can be used as vaccines.

6 Claims, 6 Drawing Sheets

(56) References Cited

OTHER PUBLICATIONS

Plate, K. H, et al., "Vascular Endothelial Growth Factor and Glioma Angiogenesis: Coordinate Induction of Vegf Receptors, Distribution of Vegf Protein and Possible In Vivo Regulatory Mechanisms," *Int J Cancer*, 1994, vol. 59, No. 4, pp. 520-529.

Rammensee, et al. "MHC ligands and peptide motifs: first listing," *Immunogenetics*, vol. 41(4), pp. 178-228 (1995).

Shibuya, M. et al., "Nucleotide sequence and expression of a novel human receptor-type tyrosine kinase gene (*flt*) closely related to the *fms* family," *Oncogene*, 1990, vol. 5, No. 4, pp. 519-524.

Zaremba et al.; "Identification of an enhancer agonist cytotoxic T lymphocyte peptide from human carcinoembryonic antigen"; 1997; *Cancer Res.*; vol. 57, pp. 4750-4757.

Adams, et al., "Prediction of binding to MHC class I molecules," *J Immunol Methods*, vol. 185(2), pp. 181-190 (Sep. 25, 1995).

Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Coulie, et al., "Cytolytic T-cell responses of cancer patients vaccinated with a MAGE antigen," *Immunol Rev.*, vol. 188, pp. 33-42 (Oct. 2002).

Fujie, et al., "A *Mage*-1-Encoded HLA-A24-Binding Synthetic Peptide. Induces Specific Anti-Tumor Cytotoxic T Lymphocytes," *Int J Cancer*, vol. 80(2), pp. 169-172 (Jan. 18, 1999).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).

Parker, et al., "Scheme for Ranking Potential HLA-A2 Binding Peptides Based on Independent Binding of Individual Peptide Side Chains," *J Immunol.*, vol. 152(1), pp. 163-175 (Jan. 1, 1994).

Rosenberg, et al., "Cancer Immunotherapy: moving beyond current vaccines," *Nat Med.*, vol. 10(9), pp. 909-915 (Sep. 2004).

Schueler-Furman, et al., "Structure—based prediction of binding peptides to MHC class I molecules: Application to a broad range of MHC alleles," *Protein Sci.*, vol. 9(9), pp. 1838-1846 (Sep. 2000).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

\* cited by examiner

US 8,663,647 B2

EPITOPE PEPTIDES DERIVED FROM VASCULAR ENDOTHELIAL GROWTH FACTOR RECEPTOR 1 AND VACCINES CONTAINING THESE PEPTIDES

This application is a division of U.S. application Ser. No. 13/040,177, filed Mar. 3, 2011, which is now U.S. Pat. No. 8,257,711 and a division of U.S. application Ser. No. 11/816, 893, filed Mar. 6, 2009, which is now U.S. Pat. No. 7,919,099 and a U.S. National Stage Application of PCT/JP2006/303352, filed Feb. 17, 2006, which claims the benefit of U.S. Provisional Application Ser. No. 60/657,527 filed Feb. 28, 2005, all of which are hereby incorporated by reference in their entirety.

REFERENCE TO SEQUENCE LISTING

This application includes a Sequence Listing as a text file named "87331-002230U.S. Pat. No. 847300_SEQLIST.txt" created Oct. 11, 2012, and containing 31,329 bytes. The material contained in this text file is incorporated by reference in its entirety for all purposes

FIELD OF THE INVENTION

The present invention relates to peptides that are extremely effective as cancer vaccines, and drugs for treating and preventing tumors, which contain these peptides.

BACKGROUND OF THE INVENTION

Tumor growth is generally limited to 1~2 mm$^3$ in the absence of a vascularized blood supply, and angiogenesis has a critical role in the invasion, growth and metastasis of tumors (Folkman, J. (2002) Semin. Oncol. 29: 15-8, Folkman, J. (1996) Nat. Med. 2: 167-8, Kerbel and Folkma, (2002). Nature Rev. Cancer. 2: 727-39, Brown et al., (1995) Hum. Pathol. 26: 86-91, Eberhard et al., (2000) Cancer Res. 60: 1388-93). It has been also shown that inhibition of tumor angiogenesis is associated with suppression of tumor progression. In order to achieve suppression of angiogenesis, a number of investigators have been examining therapeutic strategies targeting vascular endothelial growth factor (VEGF) and VEGF receptor (VEGFR), which play critical roles in regulating the process of angiogenesis. These studies have shown that tumor growth can be successfully suppressed in vitro and in vivo using monoclonal antibodies, recombinant receptors or inhibitors for signal transduction (El-Mousawi et al., (2003) J. Biol. Chem. 278: 46681-91, Stefanik et al., (2001) J. Neurooncol. 55: 91-100, Wood et al., (2000) Cancer Res. 60: 2178-89, Luttun et al., (2002) Nat. Med. 8: 831-40, Lyden et al., (2001) Nat. Med. 7: 1194-201, Lu et al., (2001) Cancer Res. 61: 7002-8). However, these strategies require frequent or continuous administration of the reagents at relatively high dose levels, which may be associated with significant inconvenience and adverse effects.

VEGF binds two related tyrosine kinase receptors, VEGFR1 (Flt-1) and VEGFR2 (KDR), which are strongly expressed on endothelial cells in tumor tissue but not in normal tissue (Risau, W. (1997) Nature. 386: 671-4, Ferrara and Davis-Smyth, (1997) Endor. Rev. 18: 4-25, Shibuya et al., (1999) Curr. Topics. Microbiol. Immunol. 237: 59-83, Plate et al., (1994) Int. J. Cancer. 59: 520-9). VEGFR1 is the first VEGF receptor to be identified (Shibuya et al., (1990) Oncogene 5: 519-24), and it interacts with VEGF (VEGF-A) and with two other members of VEGF family, VEGF-B (Olofsson et al., (1996) Proc. Natl. Acad. Sci. USA 93: 2576-81) and placenta growth factor (PlGF) (Maglione et al., 1991. Proc. Natl. Acad. Sci. USA 88: 9267-71). By displacing VEGF from VEGFR1, PlGF is expected to make more VEGF available to bind and activate VEGFR2 and thereby enhance VEGF-driven angiogenesis (Park et al., (1994) J. Biol. Chem. 269: 25646-54). Other studies have shown that a synergism exists between VEGF and PlGF in vivo, especially during pathological situations, as evidenced by impaired tumorigenesis and vascular leakage in PlGF-/- mice (Carmeliet et al., (2001) Nat. Med. 7: 575-83).

Recent reports have shown that vaccination using cDNA or recombinant protein of mouse VEGFR2 is associated with significant anti-tumor effects in mouse tumor models (Li et al., (2002) J. Exp. Med. 195: 1575-84, Niethammer et al., (2002) Nat. Med. 8: 1369-75). But these results cannot directly warrant clinical application of this strategy, since they used the mouse homologue of human VEGFR2 in mouse systems that are considered to be significantly different from the human counterpart.

ABBREVIATIONS USED IN THE PRESENT APPLICATION

CTL, cytotoxic T lymphocyte
VEGF, vascular endothelial growth factor
PlGF, placenta growth factor
VEGFR1, vascular endothelial growth factor receptor 1
VEGFR2, vascular endothelial growth factor receptor 2
TGM, transgenic mice
TAA, tumor associate antigen.
i.d., intradermal injection
s.c., subcutaneous injection
IFA, incomplete FREUND's adjuvant

BRIEF SUMMARY OF THE INVENTION

The present invention provides peptides that induce cytotoxic T cells against endothelial cells endogenously expressing VEGFR1. The peptides of the invention comprise an amino acid sequence of SEQ ID NO: 1, 2, 13 or a sequence wherein 1, 2, or several amino acids are substituted or added. In certain embodiments, the second amino acid from the N terminus is leucine or methionine. In some embodiments, the C-terminal amino acid is valine or leucine.

The present invention also provides peptides comprising the amino acid sequence of SEQ ID NO: 32, or a sequence wherein 1, 2, or several amino acids are substituted or added. In certain embodiments, the second amino acid from the N terminus is phenylalanine, tyrosine, methionine, or tryptophan. In some embodiments, the C-terminal amino acid is phenylalanine, leucine, isoleucine, tryptophan, or methionine.

The present invention further provides pharmaceutical compositions for treating or preventing tumors, wherein the composition comprises the peptides of the invention.

The present invention provides exosomes that present on their surface a complex comprising the peptide of this invention and an HLA antigen. In some embodiments, the HLA antigen is HLA-A24 (e.g., HLA A2402) or HLA-A02 (HLA-0201).

Methods of inducing antigen-presenting cells having high cytotoxic T cell inducibility and methods of inducing cytoxic T cells comprising administering the peptides of the invention to a patient are also provided. In some embodiments, the methods comprise transferring a gene comprising a polynucleotide encoding the peptide of the invention to antigen-presenting cells. The invention provided isolated cytotoxic T cells and antigen presenting cells which are induced by the methods of the invention. The present invention provides antigen-presenting cells, which comprise a complex formed between an HLA antigen and the peptide of the invention.

The present invention also provides vaccines for inhibiting angiogenesis at a diseased site, wherein the vaccine comprises the peptide of the invention as the active ingredient. The vaccine of the invention may be intended for administration to a subject whose HLA antigen is HLA-A24 or HLA-A02. In some embodiments, the vaccine is used to suppress the growth of and/or metastasis of malignant tumors.

The present invention further provides methods of treating or preventing tumors in a subject comprising administering to said subject a vaccine comprising a peptide of the invention, or an immunologically active fragment, or a polynucleotide encoding the peptide.

The invention also provides methods of treating or preventing angiogenesis-mediated disease in a subject comprising administering a vaccine of the invention. In some embodiments, the angiogenesis-mediated disease is diabetic retinopathy, chronic rheumatoid arthritis, psoriasis, or atherosclerosis.

It is to be understood that both the foregoing summary of the invention and the following detailed description are of a preferred embodiment, and not restrictive of the invention or other alternate embodiments of the invention.

DETAILED DESCRIPTION OF THE INVENTION

Figure 1:
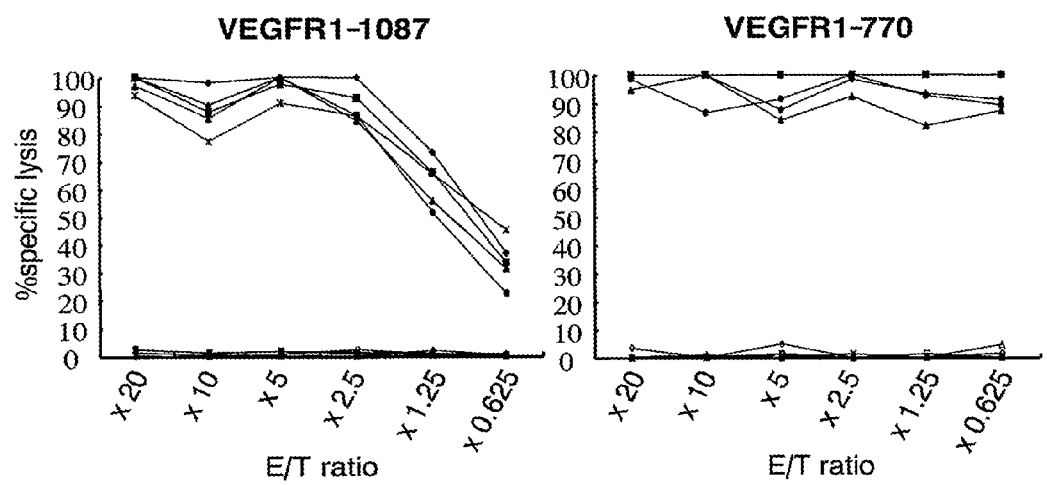
FIG. 1 is a graph showing the establishment of HLA-A*0201 restricted CTL clones using epitope candidates derived from VEGFR1. Cytotoxicity of each CTL clone against T2 cells pulsed each epitope peptide binding with HLA-A*0201. T2 cells were used for CTL responses in the presence or absence of each peptide. CTL clones showed specific cytotoxicities against the target cells pulsed with corresponding peptides. E/T ratio indicates effector/target-cell.

The words "a", "an", and "the" as used herein mean "at least one" unless otherwise specifically indicated.

Angiogenesis has been shown to be a critical mechanism for tumor progression. Multiple studies have suggested that tumor growth can be suppressed if tumor angiogenesis can be inhibited using various types of anti-angiogenic agents. In the present invention, we examined the possibility of developing novel immunotherapy targeting VEGFR1. We first identified the peptide epitopes of VEGFR1 from HLA-A2 and A24, and successfully established CTL clones with potent cytotoxicity against endothelial cells endogenously expressing VEGFR1. In A2/Kb transgenic mice, vaccination using these epitope peptides in vivo was associated with significant suppression of tumor growth in a therapeutic model. In anti-angiogenesis assay, tumor-induced angiogenesis was significantly suppressed with the vaccination. These results in vitro and in vivo strongly suggest VEGFR1 could be a promising target, and support the definitive rationale of the clinical development for anti-angiogenic immunotherapy against various kinds of cancers.

In the present invention, we examined the effectiveness of this novel immunotherapy in systems closely related to clinical settings. We identified the epitope peptides of human VEGFR1 restricted to HLA-A*0201 and A*2402 (Rammensee et al., 1995. Immunogenetics. 41: 178-228) and showed that CTLs induced with these peptides have potent and specific cytotoxicity against not only peptide-pulsed target cells but also target cells endogenously expressing VEGFR1 in an HLA class I restricted fashion. Furthermore, we examined in vivo anti-tumor effects of the vaccination with these epitope peptides using a unique mouse model that may be directly translated into the clinical setting. Our model system uses A2/Kb transgenic mice (TGM), which have been shown to be useful for the analysis of human CTL epitopes. There is approximately 71% concordance between humans and A2/Kb TGM in the CTL repertoire (Wentworth et al., (1996) Eur. J. Immunol. 26: 97-101). To construct tumor systems, we transplanted syngeneic mouse tumor cells which were chemically induced in C57BL/6 mice (H-2 Kb) not expressing HLA-A*0201 molecules. This tumor system, combining A2/Kb TGM and H-2 Kb mouse cell line, offers a unique setting. Since endothelial cells in A2/Kb TGM express HLA-A*0201 molecule, the CTLs induced by vaccination using VEGFR1 epitope peptides recognize endothelial cells which express both HLA-A*0201 and VEGFR1. Thus, in vivo anti-tumor effects of an anti-angiogenic vaccine can be evaluated in HLA-A*0201 restricted fashion. However, they do not recognize tumor cells even if they express VEGFR1 because they do not express HLA-A*0201. In this in vivo tumor model, vaccination using these epitope peptides was associated with significant suppression of the tumor growth. In an anti-angiogenesis assay, tumor-induced angiogenesis was significantly suppressed with vaccination using these epitope peptides. These results show that the vaccination using epitope peptides derived from VEGFR1 induces an antitumor-immune response.

Identification of the tumor associate antigens (TAAs) has enabled the clinical development of peptide-based cancer vaccines, which could induce CTLs and lyse tumor cells in HLA class I restricted fashion (Bruggen et al., (1991) Science. 254: 1643-7, Boon et al., (1996) J. Exp. Med. 183: 725-9, Rosenberg et al., (1998) Nat. Med. 4: 321-7, Butterfield et al., (1999) Cancer Res. 59: 3134-42). Multiple clinical trials using TAA peptides have reported that tumor regressions were observed in the melanoma patients (Rosenberg et al., (1998) Nat. Med. 4: 321-7. Nestle et al., (1998) Nat. Med. 4: 328-32, Thurner et al., (1999) J. Exp. Med. 190: 1669-78, Belli et al., (2002) J. Clin. Oncol. 20: 4169-80, Coulie et al., (2002) Immunol. Rev. 188: 33-42). It has been suggested that clinical efficacy could be effected by loss or down-regulation of HLA class I molecules on the tumor cells (Cormier et al., (1998) Int. J. Cancer. 75: 517-24, Paschen et al., (2003) Int. J. Cancer. 103: 759-67, Fonteneau et al., (1997) J. Immuol. 159: 2831-9. Reynolds et al., (1998) J. Immunol. 161: 6970-6). The frequency of tumors showing some alteration in expression of HLA class I molecules has been estimated to be more than 40% (Cormier et al., (1998) Int. J. Cancer. 75: 517-24, Paschen et al., (2003) Int. J. Cancer. 103: 759-67). Thus, significant portion of tumor cells could escape from the CTLs specific to the class I-epitope, even if CTLs could be successfully induced by cancer vaccine targeting tumor cells themselves. The development of effective vaccines against endothelial cells involved in tumor angiogenesis is an alternate approach. Endothelial cells are genetically stable, do not show down-regulation of HLA Class I molecules, and are critically involved in the progression of a variety of tumor. Furthermore, the CTLs could directly cause damage to the endothelial cells without penetrating any other tissue, and lysis of even low numbers of endothelial cells within tumor vasculature may result in destruction of vessel integrity leading to inhibition of large numbers of tumor cells (Folkman, J. (1995) Nat. Med. 1: 27-31). Therefore, endothelial cells are a good target for cancer immunotherapy. To specifically and efficiently prevent tumor-angiogenesis with CTL response, the appropriate target needs to be selected among the molecules related to angiogenesis.

VEGF binds two related tyrosine kinase receptors, VEGFR1 (Flt-1) (SEQ ID NOS:44 and 45) and VEGFR2 (KDR), which are strongly expressed on endothelial cells in tumor tissue but not in normal tissue (Risau, W. (1997) Nature. 386: 671-4, Shibuya et al., (1999) Curr. Topics. Microbiol. Immunol. 237: 59-83, Plate et al., (1994) Int. J. Cancer. 59: 520-9). Suppression of these receptors showed anti-tumor effects including neutralizing antibody, recombinant receptors or kinase inhibitors (El-Mousawi et al., (2003) J. Biol. Chem. 278: 46681-91, Stefanik et al., (2001) J. Neurooncol. 55: 91-100, Wood et al., (2000) Cancer Res. 60: 2178-89, Luttun et al., (2002) Nat. Med. 8: 831-40, Lyden et al., (2001) Nat. Med. 7: 1194-201, Lu et al., (2001) Cancer Res. 61: 7002-8). Neutralizing anti-VEGFR1 antibodies efficiently attenuated tumor growth and neovascularization with dose dependent manner (Luttun et al., (2002) Nat. Med. 8: 831-40). Furthermore, combination treatment with reagents blocking both VEGFR1 and VEGFR2 or the use of a bifunctional antibody ('diabody') against VEGFR1 and VEGFR2, as such strategies resulted in stronger inhibition of vessel growth than monotherapy with a single antibody or with the monofunctional parent antibody (Lyden et al., (2001) Nat. Med. 7: 1194-201, Lu et al., (2001) Cancer Res. 61: 7002-8).

In the present invention using our novel model systems in vitro and in vivo, we have demonstrated that an immunotherapy targeting tumor-induced angiogenesis is effective. At first, we identified the epitope peptides of VEGFR1 restricted to HLA-A*0201 and A*2402 which are frequently recognized HLA-alleles (Rammensee et al., (1995) Immunogenetics. 41: 178-228). The CTLs were successfully induced with these peptides, and they showed potent cytotoxic activities against not only peptide-pulsed target cells but also endogenously VEGFR1 expressing cells. Our findings clearly demonstrated that human VEGFR1 is immunogenic in the human system.

Then, we demonstrated in vivo anti-tumor effects using multiple tumor cell lines and A2/Kb TGM, a good model system to evaluate immune responses in humans against tumor cells with the loss of HLA class I expression. It has been shown that there is approximately 71% concordance between the CTL repertoire of human and A2/Kb TGM (Wentworth et al., (1996) Eur. J. Immunol. 26: 97-101). Thus, CTLs induced by vaccination using epitope peptides could recognize endothelial cells, which are derived from A2/Kb TGM and express VEGFR1 and HLA-A*0201, but do not recognize the tumor cells which have no "human" MHC class I molecules. Using this unique tumor model system, significant inhibition of the tumor growth was observed with vaccination using these epitope peptides. This peptide-based vaccine was also associated with significant suppression of tumors before the vaccination as well. These results show that our vaccination strategy is effective even for tumors with HLA deficit, which is considered to be one of the escape mechanisms of tumors. We have also shown in a DAS assay that tumor-induced angiogenesis was significantly inhibited with vaccination using these epitope peptides. This result shows that the inhibition of tumor angiogenesis can be achieved with peptide vaccination targeting the molecule expressed on tumor-induced vascular endothelial cells.

These results, in vitro and in vivo, show that VEGFR1 is a useful target of immunological therapy using cellular immunity and support the definitive rationale of the clinical development of this strategy against a broad range of cancers.

Regarding HLA antigens, the data presented here show that the uses of A-24 type or A-02 type (which are said to be highly expressed among the Japanese) are favorable for obtaining effective results. The uses of subtypes such as A-2402 and A-0201 are even more preferable. However, in the clinic, the type of HLA antigen of the patient requiring treatment is investigated in advance, which enables appropriate selection of peptides having high levels of binding affinity to this antigen, or having cytotoxic T cell (CTL) inducibility by antigen presentation. Furthermore, in order to obtain peptides showing high binding affinity and CTL inducibility, substitution or addition of 1, 2, or several amino acids may be performed based on the amino acid sequence of the naturally occurring VEGFR1 partial peptide. Herein, the term "several" means 5 or less, or preferably 3 or less. Furthermore, in addition to peptides that are naturally displayed, since the regularity of the sequences of peptides displayed by binding to HLA antigens is already known (Kubo R T, et al., (1994) J. Immunol., 152, 3913-24; Rammensee H G, et al., (1995) Immunogenetics. 41:178-228; Kondo A, et al., (1994) J. Immunol. 155:4307-12), modifications based on such regularity can be performed on the obtained peptides. For example, peptides showing high HLA-24 binding affinity have their second amino acid from the N terminus substituted with phenylalanine, tyrosine, methionine, or tryptophan, and peptides whose amino acid at the C terminus is substituted with phenylalanine, leucine, isoleucine, tryptophan, or methionine may also be used favorably. On the other hand, peptides showing high HLA-0201 binding affinity have their second amino acid from the N terminus substituted with leucine or methionine, and peptides whose C-terminal amino acid is substituted with valine or leucine may be used favorably. Furthermore, 1 to 2 amino acids may be added to the N terminus and/or C terminus of the peptide.

However, when the peptide sequence is identical to a portion of the amino acid sequence of an endogenous or exogenous protein having a different function, side effects such as autoimmune disorders or allergic symptoms against specific substances may be induced, therefore, preferably, situations in which the sequence matches the amino acid sequence of another protein is avoided by performing a homology search using available databases. Furthermore, if it is clear from homology searches that not even peptides in which 1 or 2 amino acids are different exist, there is no danger that modifications of the above-mentioned amino acid sequence in order to increase the binding affinity with HLA antigens, and/or increase the CTL inducibility will cause such problems.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. Confirmation of CTL inducibility is accomplished by inducing antigen-presenting cells carrying human MHC antigens (for example, B-lymphocytes, macrophages, and dendritic cells), or more specifically dendritic cells derived from human peripheral blood mononuclear leukocytes, and after stimulation with the peptides, mixing with CD8-positive cells, and then measuring the cytotoxic activity against the target cells. As the reaction system, transgenic animals that have been produced to express a human HLA antigen (for example, those described in BenMohamed et al., (2000) Hum. Immunol.; 61(8):764-79 Related Articles, Books, Linkout) may be used. For example, the target cells can be radiolabeled with $^{51}Cr$ and such, and cytotoxic activity can be calculated from radioactivity released from the target cells. Alternatively, it can be examined by measuring IFN-γ produced and released by CTL in the presence of antigen-presenting cells that carry immobilized peptides, and visualizing the inhibition zone on the media using anti-IFN-γ monoclonal antibodies.

As a result of examining the CTL inducibility of peptides as described above, those having high binding affinity to an HLA antigen did not necessarily have high inducibility. Furthermore, nonapeptides or decapeptides selected from peptides comprising the amino acid sequences indicated by VLLWEIFSL (SEQ ID NO: 1), TLFWLLLTL (SEQ ID NO: 2), NLTATLIVNV (SEQ ID NO: 13), SYGVLLWEIF (SEQ ID NO: 32) showed particularly high CTL inducibility.

Furthermore, the present invention provides immunogenic peptides of less than about 40 amino acids, often less than about 20 amino acids, usually less than about 15 amino acids having cytotoxic T cell inducibility, and comprising the amino acid sequence of SEQ ID NO: 32 in which 1, 2, or several amino acids are substituted or added. In some preferred embodiments, the immunogenic peptide has an amino acid sequence comprising 10 amino acids indicated in SEQ ID NO: 32 in which 1, 2, or several amino acids are substituted or added may have CTL inducibility as long as it does not match the amino acid sequence of other proteins. In particular, amino acid substitution to phenylalanine, tyrosine, methionine, or tryptophan at the second amino acid from the N terminus, and to phenylalanine, leucine, isoleucine, tryptophan, or methionine at the C-terminal amino acid, and amino acid addition of 1 to 2 amino acids at the N terminus and/or C terminus are favorable examples. One of skill will recognize that in addition to amino acid substitutions and additions, immunologically active fragments of the peptides may also be used in the methods of the invention. Methods for determining active fragments are well known in the art.

The present invention also provides peptides having cytotoxic T cell inducibility, and comprising the amino acid sequence of SEQ ID NOS: 1, 2, or 13, in which 1, 2, or several amino acids are substituted or added. The amino acid sequence comprising 9 or 10 amino acids indicated by SEQ ID NOS: 1, 2, or 13 in which 1, 2, or several amino acids are substituted or added may have CTL inducibility as long as it does not match the amino acid sequence of other proteins. In particular, amino acid substitution to leucine, or methionine at the second amino acid from the N terminus, and to valine, or leucine at the C-terminal amino acid, and amino acid addition of 1 to 2 amino acids at the N terminus and/or C terminus are favorable examples. One of skill will recognize that in addition to amino acid substitutions and additions, immunologically active fragments of the peptides may also be used in the methods of the invention. Methods for determining active fragments are well known in the art. CTL clones obtained by stimulation by these modified peptides can recognize the original peptides and cause damage.

Peptides of the invention can be prepared using well known techniques. For example, the peptides can be prepared synthetically, by recombinant DNA technology or chemical synthesis. Peptide of the invention may be synthesized individually or as longer polypeptides comprising two or more peptides. The peptide are preferably isolated i.e., substantially free of other naturally occurring host cell proteins and fragments thereof.

The peptides may contain modifications such as glycosylation, side chain oxidation, or phosphorylation; so long as the modifications do not destroy the biological activity of the peptides as described herein. Other modifications include incorporation of D-amino acids or other amino acid mimetics that can be used, for example, to increase serum half life of the peptides.

The peptides of this invention can be prepared into a combination, which comprises 1 or more peptides of the invention, for use as a cancer vaccine that may induce CTL in vivo or ex vivo. The peptides may be in a cocktail or may be conjugated to each other using standard techniques. For example, the peptides can be expressed as a single polypeptide sequence. The peptides in the combination may be the same or different. By administering the peptides of this invention, the peptides are presented at a high density on the HLA antigens of antigen-presenting cells, then CTL that specifically react toward the complex formed between the displayed peptide and the HLA antigen are induced, and strong immune response against vascular endothelial cells in the tumor cells is induced. Alternatively, antigen presenting cells that have immobilized the peptides of this invention on their cell surface are obtained by removing dendritic cells from the subjects, these are stimulated ex vivo by the peptides of this invention, CTL are induced in the subjects by readministering these cells to the subjects, and as a result, aggressiveness towards the target cells can be increased.

More specifically, the present invention provides immunogenic compositions for treating tumors or preventing proliferation, metastasis, and the like of tumors. The compositions comprise 1 or more peptides of this invention. The peptides may be the same or different in the compositions. Furthermore, angiogenesis at the pathologic site is closely linked to tumors, as well as diseases such as diabetic retinopathy, chronic rheumatoid arthritis, psoriasis, and atherosclerosis, and also to metastasis of solid tumors (Folkman, J., (1995) Nature Med. 1:27-31; Bicknell et al., (1996) Curr. Opin. Oncol. 8:60-5). Therefore, the peptides of this invention can be used for treating tumors, angiogenesis-mediated disease such as diabetic retinopathy, chronic rheumatoid arthritis, psoriasis, and atherosclerosis, as well as metastasis of solid tumors.

The peptides of this invention were found to inhibit the formation of tortuous blood vessels, which are morphologically different from normal blood vessels and are formed in malignant tumor tissues, and results of analyzing wound healing and fertility in vaccinated mice confirmed that there are no adverse effects on normal physiological angiogenesis. Furthermore, when cytotoxicity against non-proliferative or proliferative endothelial cells was tested in vitro using CTL clones that recognize the peptides of this invention, these clones were found to show stronger activity towards proliferative endothelial cells than towards non-proliferative endothelial cells. More specifically, they function very specifically to disorders in which proliferative endothelial cells are observed, and particularly to cancer.

In vivo and in vitro stimulation of dendritic cells by the peptides of this invention can be performed easily by exposing the cells to a high concentration of the peptides so that these peptides exchange with peptides that were originally immobilized on the cells. Therefore, the peptides used in this invention must have at least a certain level of binding affinity to HLA antigens.

The peptides of this invention can be administered directly or as a pharmaceutical composition that has been formulated by conventional formulation methods. In such cases, in addition to the peptides of this invention, carriers, excipients, and such that are ordinarily used for drugs can be included as appropriate without particular limitations. The immunogenic compositions of this invention may be used for treatment and prevention of various tumors such as gastric cancer, duodenal cancer, colon cancer, lung cancer, breast cancer, prostate cancer, and brain tumor. The peptides of this invention targets the endothelial cells of blood vessels that are newly formed in tumor tissues, and do not target the tumor cells themselves, therefore, a wide variety of tumors become targets of treatment, and there are no particular limitations to their use.

Immunogenic compositions for treatment and/or prevention of tumors, which comprise the peptides of this invention as the active ingredients, can be administered with an adjuvant so that cellular immunity will be established effectively, or they may be administered with other active ingredients such as antitumor agents, and they may be administered by formulation into granules. An adjuvant that may be applied includes those described in the literature (Johnson A G. (1994) Clin. Microbiol. Rev., 7:277-89). Exemplary adjuvants include, aluminum phosphate, aluminum hydroxide, or alum. Furthermore, liposome formulations, granular formulations in which the drug is bound to few μm diameter beads, and formulations in which a lipid is bound to the drug may be conveniently used. The method of administration may be oral, intradermal, subcutaneous, intravenous injection, or such, and systemic administration or local administration to the vicinity of the targeted tumor is possible. The dose of the peptides of this invention can be adjusted appropriately according to the disease to be treated, age of the patient, weight, method of administration, and such, and is ordinarily 0.001 mg to 1000 mg, preferably 0.01 mg to 100 mg, more preferably 0.1 mg to 10 mg, and is preferably administered once in a few days to few months. One skilled in the art can appropriately select the suitable dose.

Alternatively, the present invention provides intracellular vesicles called exosomes, which present complexes formed between the peptides of this invention and HLA antigens on their surface. Exosomes can be prepared, for example by using the methods described in detail in Published Japanese Translation of International Publication Nos. Hei 11-510507 and 2000-512161, and is preferably prepared using antigen presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, for a Japanese, HLA-A24 or HLA-A02, particularly HLA-A2402 or HLA-0201 is often appropriate.

In some embodiments the vaccine compositions of the invention comprise a component which primes cytotoxic T lymphocytes. Lipids have been identified as agents capable of priming CTL in vivo against viral antigens. For example, palmitic acid residues can be attached to the ε- and α-amino groups of a lysine residue and then linked to an immunogenic peptide of the invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinlyseryl-serine (P3CSS) can be used to prime CTL when covalently attached to an appropriate peptide (see, e.g., Deres, et al., (1989) Nature 342:561-4).

The immunogenic compositions of the invention may also comprise nucleic acids encoding the immunogenic peptides disclosed here. See, e.g., Wolff et al., (1990) Science 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover, et al., (1991) Nature 351:456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata, et al., (2000) Mol. Med. Today 6:66-71; Shedlock, et al., (2000) J. Leukoc. Biol. 68:793-806; and Hipp, et al., (2000) In vivo 14:571-85.

The present invention also provides methods of inducing antigen-presenting cells using the peptides of this invention. The antigen-presenting cells can be induced by inducing dendritic cells from the peripheral blood monocytes and then contacting (stimulating) them with the peptides of this invention in vitro or in vivo. When the peptides of this invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine.

This invention also provides a method for inducing antigen-presenting cells having a high level of cytotoxic T cell inducibility, in which the method comprises the step of transferring genes comprising polynucleotides that encode the peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be used. More specifically, it may be performed as described in Reeves M E, et al., (1996) Cancer Res., 56:5672-7; Butterfield L H, et al., (1998) J. Immunol., 161: 5607-13; Boczkowski D, et al., (1996) J. Exp. Med., 184:465-72; Published Japanese Translation of International Publication No. 2000-509281. By transferring the gene into antigen-presenting cells, the gene undergoes transcription, translation, and such in the cell, and then the obtained protein is processed and binded to MHC Class I or Class II, and proceeds through a presentation pathway to present partial peptides.

Furthermore, the present invention provides methods for inducing CTL using the peptides of this invention. When the peptides of this invention are administered to a subject, CTL is induced in the body of the subject, and the strength of the immune system targeting the angiogenic endothelial cells in the tumor tissues is enhanced. Alternatively, they may be used for an ex vivo therapeutic method, in which subject-derived antigen-presenting cells, and CD8-positive cells, or peripheral blood mononuclear leukocytes are contacted (stimulated) with the peptides of this invention in vitro, and after inducing CTL, the cells are returned to the subject.

Furthermore, the present invention provides isolated cytotoxic T cells that are induced using the peptides of this invention. The cytotoxic T cells, which have been induced by stimulation from antigen-presenting cells that present the peptides of this invention, are preferably derived from subjects who are targets of treatment and/or prevention, and can be administered by themselves or in combination with other drugs including the peptides of this invention or exosomes for the purpose of antitumor effects. The obtained cytotoxic T cells act specifically against target cells presenting the peptides of this invention, or preferably the same peptides used for induction. The target cells may be cells that express VEGFR1 endogenously, or cells that are transfected with a gene that encodes VEGFR1, and cells that present the peptides of this invention on the cell surface due to stimulation by these peptides can also become targets of attack.

The present invention also provides antigen-presenting cells that comprise presentation of complexes formed between HLA antigens and the peptides of this invention. The antigen-presenting cells that are obtained by contacting the peptides of this invention, or the nucleotides encoding the peptides of this invention are preferably derived from subjects who are the targets of treatment and/or prevention, and can be administered as vaccines by themselves or in combination with other drugs including the peptides of this invention, exosomes, or cytotoxic T cells.

In the present invention, the phrase "vaccine" (also referred to as an immunogenic composition) refers to a substance that has the function to induce immunity against tumor endothelial cells to suppress tumors upon inoculation into animals. According to the present invention, polypeptides comprising the amino acid sequence of SEQ ID NO: 1, 2, 13 were suggested to be HLA-A02 restricted epitope peptides and SEQ ID NO: 32 was suggested to be HLA-A24 restricted epitope peptides that may induce potent and specific immune response against tumor endothelial cells expressing VEGFR1. Thus, the present invention also encompasses method of inducing anti-tumor immunity using polypeptides comprising the amino acid sequence of SEQ ID NO: 1, 2, 13, 32. In general, anti-tumor immunity includes immune responses such as follows:

induction of cytotoxic lymphocytes against endothelial cells in tumors, induction of antibodies that recognize endothelial cells in tumors, and induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor endothelial cells are useful as vaccines against tumors. Furthermore, APC that acquired the ability to induce CTL against tumor endothelial cells by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth, proliferation or metastasis of tumor cells is suppressed by those antibodies, the polypeptide can be determined to have an ability to induce anti-tumor immunity.

The present invention also relates to a method of treating or preventing tumors in a subject comprising administering to said subject a vaccine comprising a polypeptide encoded by a nucleic acid selected from the group consisting of VEGFR1 or an immunologically active fragment of said polypeptide, or a polynucleotide encoding the polypeptide or the fragment thereof. Administration of the polypeptide induces an anti-tumor immunity in a subject. Thus, the present invention further provides a method for inducing anti tumor immunity. The polypeptide or the immunologically active fragments thereof are useful as vaccines against tumors. In some cases the proteins or fragments thereof may be administered in a form bound to the T cell receptor (TCR) or presented on an antigen presenting cell (APC), such as macrophage, dendritic cell (DC) or B-cells. Due to the strong antigen presenting ability of DC, the use of DC is most preferable among the APCs.

Anti-tumor immunity is induced by administering the vaccine of this invention, and the induction of anti-tumor immunity enables treatment and prevention of tumors. Therapy against or prevention of the onset of tumors includes any of the steps, such as inhibition of the growth of tumors cells, involution of tumors cells and suppression of occurrence of tumors cells. Decrease in mortality of individuals having tumors, decrease of tumors markers in the blood, alleviation of detectable symptoms accompanying tumors and such are also included in the therapy or prevention of tumors. Such therapeutic and preventive effects are preferably statistically significant. For example, in observation, at a significance level of 5% or less, wherein the therapeutic or preventive effect of a vaccine against tumors is compared to a control without vaccine administration. For example, Student's t-test, the Mann-Whitney U-test or ANOVA may be used for statistical analyses.

The above-mentioned protein having immunological activity, or a polynucleotide or vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications, and publications cited herein are incorporated by reference.

EXAMPLES

The present invention is illustrated in details by following Examples, but is not restricted to these Examples.

Materials and Methods

Cell Lines

The T2 cell line was generously provided by Dr. H. Shiku (Mie University School of Medicine). The AG1-G1-Flt-1 and AG1-G1-Neo cell lines were kindly provided by Dr. M. Shibuya (Institute of Medical Science, The University of Tokyo). The AG1-G1 cell line was established from human benign hemangioma, and AG1-G1-Flt-1 was generated infecting the AG1-G1 cell lines with the BCMGS plasmid vector carrying VEGFR1 cDNA. MCA205, a methylcholanthrene-induced murine fibrosarcoma cell line, was generous gifts from Dr. S. A. Rosenberg (National Cancer Institute, Bethesda, Md.). B16, a murine melanoma, and MC38, a murine colon adenocarcinoma were purchased from ATCC.

Synthetic Peptides

The candidates of VEGFR1 derived epitope peptides restricted to HLA-A*0201 (A2) and -A*2402 (A24) were selected based on the binding affinities to the corresponding HLAs. The binding affinities were predicted with the website of BioInformatics & Molecular Analysis Section (BIMAS) (Kuzushima et al., (2003) Blood. 101: 1460-8, Parker et al., (1994) J. Immunol. 152: 163-75). These candidate peptides were synthesized by Sawady Technology, Japan according to the standard solid phase synthesis method and purified by reversed phase HPLC. The purity (>95%) and the identity of the peptides were determined by analytical HPLC and mass spectrometry analysis, respectively. The peptides used in the present invention are listed in Table 1 and 2.

CEA peptide (DVLYGPDTPI (SEQ ID NO. 41)) was used as a positive control for in vivo mouse model. CMV peptides (A02; NLVPMVATV (SEQ ID NO. 42), A24; QYDPVAALF (SEQ ID NO. 43)) were used as positive controls for human CTL induction in vitro (Solache et al., (1999) J. Immunol. 163: 5512-8, Kuzushima et al., (2001) Blood. 98: 1872-81).

Animals

The A2/Kb TGM, of which MHC class I consists of α1 and α2 domain of HLA-A*0201 and α3 domain of mouse H-2 Kb, were prepared as described elsewhere (Wentworth et al., (1996) Eur. J. Immunol. 26: 97-101). The animals were maintained in the specific-pathogen-free Animal Facility of the Institute of Medical Science, The University of Tokyo, and all the protocols for animal experiments were approved by the ethical committee of our institute.

Generation of CTL Lines and Clones

Monocyte-derived dendritic cells (DCs) were used to induce CTL responses against peptides presented on HLA as previously described (Nukaya et al., (1999) Int. J. Cancer. 80: 92-7, Tsai et al., (1997) J. Immunol. 158: 1796-802, Nakahara et al., (2003) Cancer Res. 63: 4112-8). In brief, the PBMCs were obtained from the healthy volunteers with corresponding HLAs and cultured in the presence of GM-CSF (provided by Kirin Brewery Company, Japan) and IL-4 (Genzyme/Techne, Minneapolis). After culture for 5 days, OK-432 (Chugai Pharmaceutical Corporation, Japan) was added to the culture to obtain mature DCs (Nakahara et al., (2003) Cancer Res. 63: 4112-8). On day 7, generated mature DCs were pulsed with each peptide for T cell stimulation. Using these peptide-pulsed DCs each time, the autologous CD8+ T cells were stimulated for three times on day 0, 7 and 14, and then the resultant lymphoid cells were tested for their cytotoxic activities on day 21.

To generate CTL clones, established CTL lines were plated in 96-well plates at 0.3, 1, and 3 cells per well with allogenic PBMCs and A3-LCL as stimulator cells. Cytotoxic activities of resulting CTL clones were tested on the 14th day.

Cytotoxicity Assay

Cytotoxic activities were measured using a standard 4-h $^{51}$Cr-release assay. The T2 cells and A24-LCL were used as target cells pulsed with candidate peptides. Percent specific lysis was calculated as follows:

% Specific lysis=[(experimental release−spontaneous release)/(maximum release−spontaneous release)]×100.

Immunogenicity of Epitope Peptides in A2/Kb TGM

For priming the peptide-specific CTLs, immunization was given using 200 μl of vaccine mixture, which contains 100 μg of an HLA-A2 restricted peptide and 100 μl of IFA per mouse. The vaccine was injected intradermally in the right flank for the first immunization on day 0 and in the other flank for the second on day 11. On day 21, splenocytes of the vaccinated mice were used as the responder cells, and T2 cells pulsed with or without peptides were used as the stimulator cells for ELISPOT assay.

In Vivo Angiogenesis Assay

We examined the effects of peptide vaccination using dorsal air sac (DAS) assay which was designed to measure in vivo angiogenesis induced by tumor cells as previously described (Oikawa et al., (1997) Anticancer Res. 17: 1881-6). In brief, the A2/Kb TGM were vaccinated twice with 1-week interval in the left flank using IFA conjugated corresponding peptides as previously described with some modification (Schuler et al., (1997) J. Exp. Med. 186: 1183-7, Song et al., (1997) J. Exp. Med. 186: 1247-56, Specht et al., (1997) J. Exp. Med. 186: 1213-21). Millipore chamber (Millipore Corporation, Bedford, Mass.) was filled with PBS containing MC38 cells ($1 \times 10^6$ cells) and implanted in the dorsum of anesthetized mice on day 0. The implanted chambers were removed from s.c. fascia on day 6 and then black rings were placed at the sites exposed to a direct contact with the chamber. The angiogenic response was assessed with photographs taken using a dissecting microscope. The extent of angiogenesis was determined with the number of newly formed blood vessels of >3 mm in length and scored semi quantitatively using an index ranging from 0 (none) to 5 (many).

In Vivo Anti-Tumor Effects

We examined the anti-tumor effects of this vaccination with a therapeutic model. The $1 \times 10^5$ MCA205 cells or the $5 \times 10^5$ B16 cells were injected i.d. in the right flank on day 0, and vaccination was performed on day 4 and day 14 using IFA conjugated corresponding peptides.

Statistical Analysis

Each experiment was performed in triplicate to confirm reproducibility of the results, and representative results are shown. Student's t test was used to examine the significance of the data, when applicable. The difference was considered to be statistically significant when P value was less than 0.05.

Results

HLA Class I Binding Predicted Peptides from VEGFR1 Protein

The candidates of VEGFR1 derived epitope peptides restricted to HLA-A*0201 (A2) and -A*2402 (A24) were selected based on the binding affinities to the corresponding HLAs. The binding affinities were predicted with the website of BioInformatics & Molecular Analysis Section (BIMAS).

HLA Peptide Binding Prediction software:

(//bimas.dcrt.nih.gov/cgi-bin/molbio/ken_parker_combo-form)

Kuzushima, K., et al., (2003) Blood. 101: 1460-8.

Parker, K. C., et al., (1994) J. Immunol. 152: 163-75.

Establishment of CTL Clones Using Epitope Candidates Derived from VEGFR1

We first tested the immunogenicity of VEGFR1 to determine the epitope peptides. Epitope-candidate peptides were selected in the order of the binding scores reflecting binding affinity of the peptide to the HLA class I molecules (Table 1, Table 2).

TABLE 1

HLA-A*0201 binding predicted peptides from VEGFR1 protein

| Start Position | Sequence (9mer) | SEQ ID No. | Binding affinity | Start position | Sequence (10mer) | SEQ ID No. | Binding affinity |
|---|---|---|---|---|---|---|---|
| 1087 | VLLWEIFSL | 1 | 1793 | 1153 | KLGDLLQANV | 11 | 998 |
| 770 | TLFWLLLTL | 2 | 182 | 1029 | LLSENNVVKI | 12 | 167 |
| 1028 | ILLSENNVV | 3 | 179 | 417 | NLTATLIVNV | 13 | 160 |

TABLE 1-continued

HLA-A*0201 binding predicted peptides from VEGFR1 protein

| Start Position | Sequence (9mer) | SEQ ID No. | Binding affinity | Start position | Sequence (10mer) | SEQ ID No. | Binding affinity |
|---|---|---|---|---|---|---|---|
| 766 | CVAATLFWL | 4 | 137 | 1094 | SLGGSPYPGV | 14 | 104 |
| 874 | ALMTELKIL | 5 | 75 | 1104 | QMDEDFCSRL | 15 | 96 |
| 861 | KMLKEGATA | 6 | 47 | 1086 | GVLLWEIFSL | 16 | 92 |
| 875 | LMTELKILT | 7 | 38 | 797 | IIMDPDEVPL | 17 | 76 |
| 881 | ILTHIGHHL | 8 | 36 | 1004 | FQVARGMEFL | 18 | 62 |
| 1027 | NILLSENNV | 9 | 35 | 220 | YLTHRQTNTI | 19 | 48 |
| 220 | YLTHRQTNT | 10 | 34 | 590 | ILLRTVNNRT | 20 | 47 |

TABLE 2

HLA-A*2402 binding predicted peptides from VEGFR1 protein

| Start position | Sequence (9mer) | SEQ ID No. | Binding affinity | Start position | Sequence (10mer) | SEQ ID No. | Binding affinity |
|---|---|---|---|---|---|---|---|
| 913 | KYGNLSNYL | 21 | 576 | 919 | NYLKSKRDLF | 31 | 150 |
| 919 | NYLKSKRDL | 22 | 300 | 1084 | SYGVLLWEIF | 32 | 120 |
| 871 | EYKALMTEL | 23 | 264 | 1001 | SYSFQVARGM | 33 | 35 |
| 1212 | RYVNAFKFM | 24 | 90 | 880 | KILTHIGHHL | 34 | 17 |
| 1084 | SYGVLLWEI | 25 | 66 | 1003 | SFQVARGMEF | 35 | 17 |
| 1146 | RFAELVEKL | 26 | 64 | 1212 | RYVNAFKFMS | 36 | 15 |
| 821 | EFARERLKL | 27 | 22 | 700 | KIQQEPGIIL | 37 | 12 |
| 754 | KSNLELITL | 28 | 12 | 873 | KALMTELKIL | 38 | 12 |
| 819 | KWEFARERL | 29 | 12 | 1149 | ELVEKLGDLL | 39 | 9 |
| 814 | PYDASKWEF | 30 | 11 | 1079 | KSDVWSYGVL | 40 | 8 |

We generated CTLs using these peptides and PBMCs given from healthy volunteers with HLA-A*0201 and HLA-A*2402 as described in "Materials and Methods", and CTL clones were successfully established.

Figure 2:
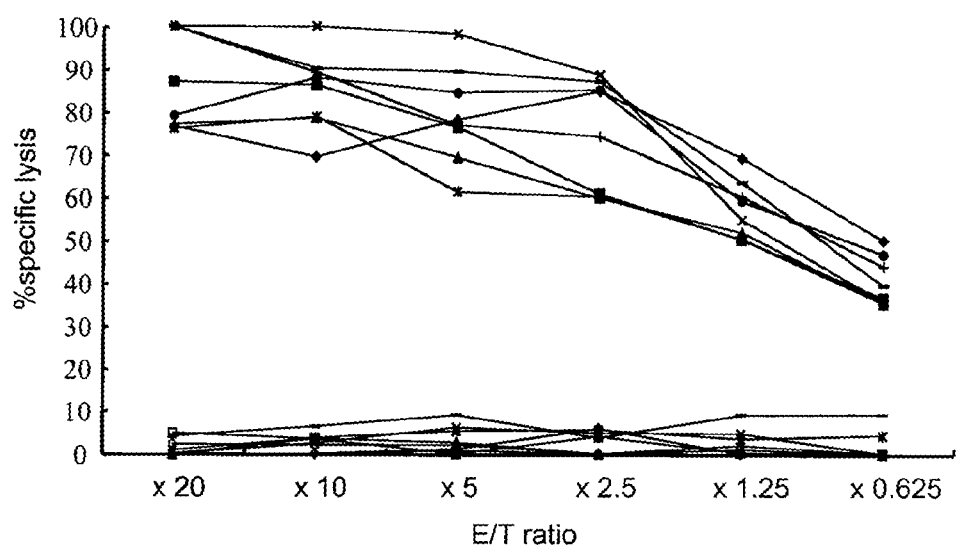
FIG. 2 is a graph showing the establishment of HLA-A*2402 restricted CTL clones using epitope candidates derived from VEGFR1. A24-LCL cells were used for CTL responses restricted to HLA-A*2402 in the presence or absence of each peptides binding with HLA-A*2402. CTL clones showed specific cytotoxicities against the target cells pulsed with corresponding peptides. E/T ratio indicates effector/target-cell.

These CTL clones showed specific cytotoxicity against the target cells pulsed with corresponding peptides (FIG. 1, FIG. 2).

We also examined the ability of established CTL clones induced with these peptides to lyse the target cells endogenously expressing VEGFR1 as well.

Figure 3:
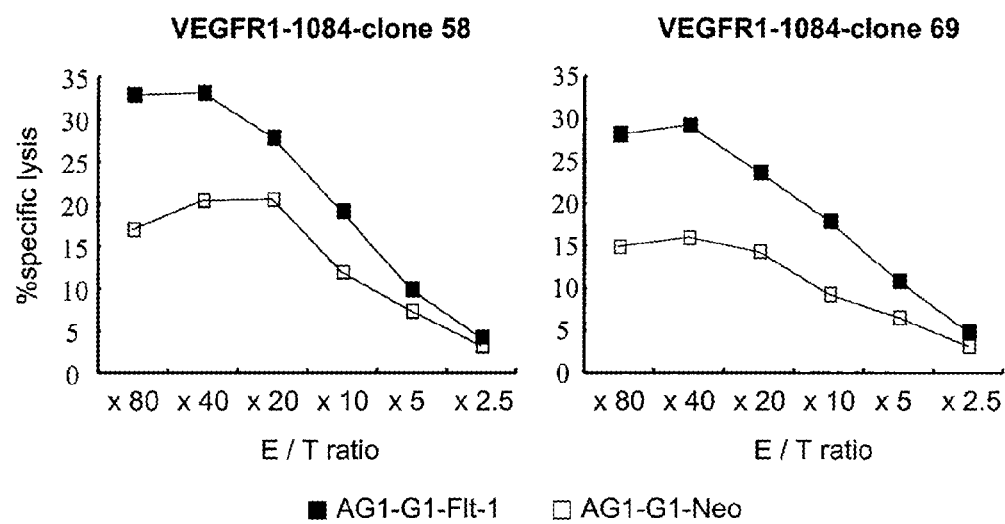
FIG. 3 is a graph showing the cytotoxicity against endogeneously VEGFR1 expressing cells. HLA-A*2402 CTL clone was examined for the cytotoxicity against VEGFR1 expressing cells (AG1-G1-Flt-1) and control (AG1-G1) with a 4-hr $^{51}$Cr-release assay. These CTL clones showed the cytotoxicities against AG1-G1-Flt-1, but not against AG1-G1. E/T ratio indicates effector/target-cell.

HLA-A*2402 CTL clone was examined for the cytotoxicity against VEGFR1 expressing cells (AG1-G1-Flt-1) and control (AG1-G1) with a 4-hr $^{51}$Cr-release assay. These CTL clones showed the cytotoxicities against AG1-G1-Flt-1, but not against AG1-G1 (FIG. 3). The cytotoxicity was significantly blocked with mAbs against CD8 and HLA-class I, but was not blocked using mAbs against CD4 nor HLA-class II (data not shown).

In Vivo Anti-Angiogenesis and Anti-Tumor Effects Associated with the Vaccination Using VEGFR1-Epitope Peptides.

We tested in vivo anti-angiogenesis effects and anti-tumor effects of vaccination with VEGFR1-epitope peptides using A2/Kb TGM.

Figure 4:
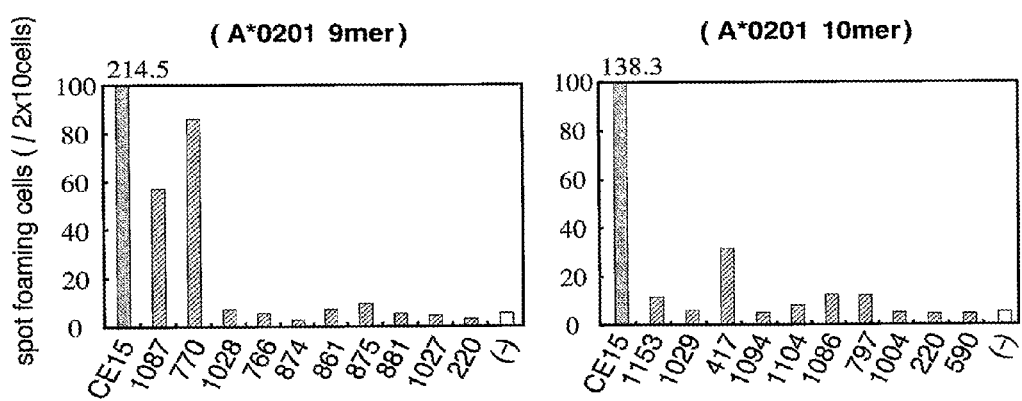
FIG. 4 is a graph showing the results of in vivo CTL response associated with the vaccination using VEGFR1-epitope peptides by IFN-γ ELISPOT assay. IFA-conjugated peptides were injected i.d. into A2/Kb TGM on day 0 and day 11. On day 21, splenocytes of the vaccinated mice were used as the responder cells, and T2 cells pulsed with or without peptides were used as the stimulator cells for ELISPOT assay. Specific production of IFN-γ for the corresponding peptide was observed in the mice vaccinated with VEGFR1-1087, -770, -417 peptides. (E/T ratio: ×20).

At first, we evaluated the immunogenicity of the epitope peptides for A2/Kb TGM to examine the specific production of IFN-γ of the CTLs induced with these peptides by ELISPOT assay (FIG. 4). IFA-conjugated peptide was injected s.c. into A2/Kb TGM on day 0 and day 11. On day 21, splenocytes of the vaccinated mice were harvested and used as the responder cells, and T2 cells pulsed with or without peptides were used as the stimulator cells for ELISPOT assay. Specific production of IFN-γ for the corresponding peptide was observed in the mice vaccinated with VEGFR1-1087, -770, -417 peptides. In this ELISPOT assay using A2/Kb TGM system, positive results were shown for the epitope peptides identified using human PBMCs.

Figure 5:
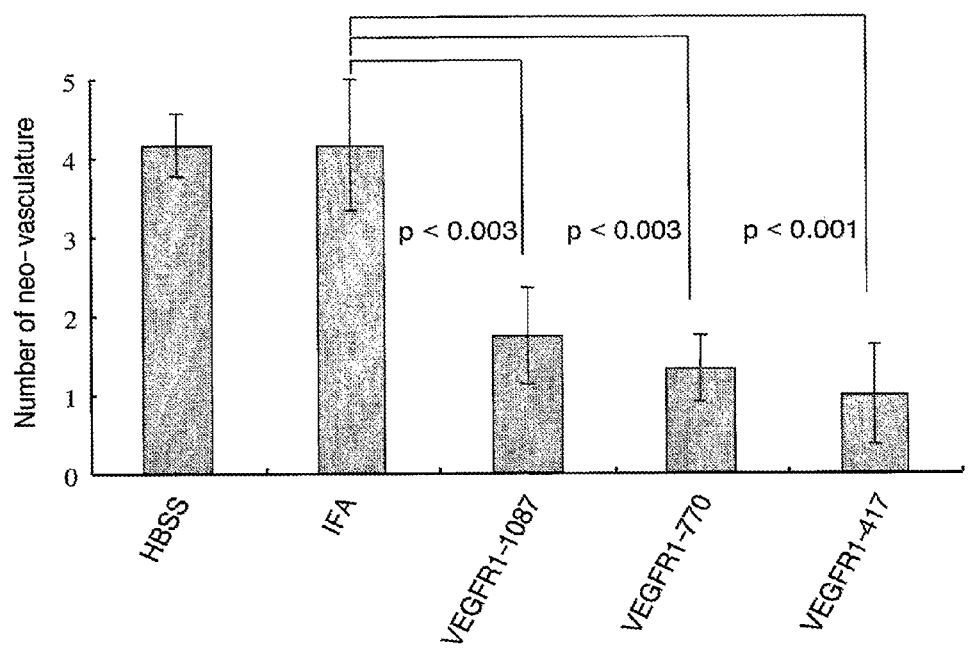
FIG. 5 is a graph showing the results of in vivo inhibition of tumor-induced angiogenesis. The angiogenic responses induced by MC38 cells in A2/Kb TGM. The mice were vaccinated twice with HBSS, IFA alone, and VEGFR1-peptide conjugated with IFA (VEGFR1-1087, -770, -417). Differences were visible macroscopically in the implanted chambers removed from s.c. fascia of vaccinated mice. Quantification of newly formed vessels in the angiogenic response. Significant inhibition of tumor-induced angiogenesis was observed in mice vaccinated with VEGFR1-1087, -770, -417 peptides. Error bar indicate s.e.

We examined whether the vaccination using peptide derived from VEGFR1 suppress the tumor-induced angiogenesis. To confirm the effects of the peptide vaccination on angiogenesis induced by tumor cells, we employed dorsal air sac assay (DAS assay) which visualizes the extent of neovascularization in vivo. In this semiquantitative assay, significant inhibition on angiogenesis was observed in the mice vaccinated with VEGFR1-1087, -770, -417 peptides (FIG. 5).

Figure 6:
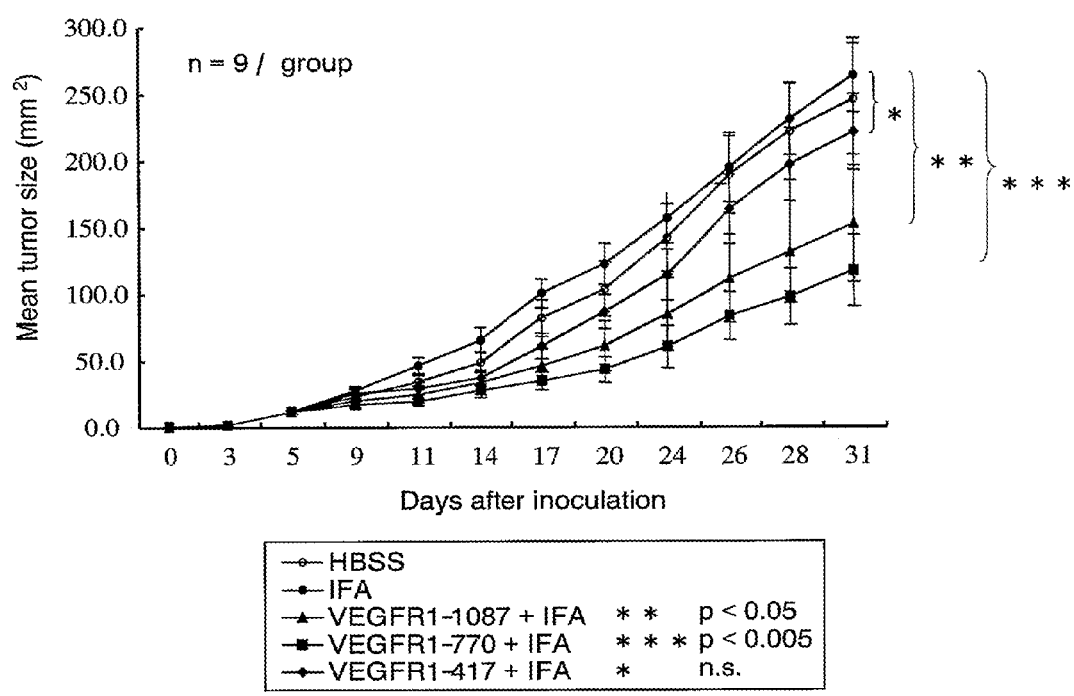
FIG. 6 is a graph showing the results of in vivo anti-tumor effect. A2/Kb TGM was inoculated i.d. with MCA205 cells. HBSS, IFA only, and IFA conjugated with VEGFR1-1087, -770, -417 peptides were vaccinated 4 days and 11 days later (the indicated arrow). Significant suppression of tumor growth was observed with the vaccination using VEGFR1-1087, -770 peptides conjugated with IFA.

The vaccination using the epitope peptide showed strong antitumor effect in therapeutic model. The MCA205, a methylcholanthrene-induced murine fibrosarcoma cell line were injected i.d. into A2/Kb TGM on day 0, and vaccination was performed on these mice on 4 and 14 days after the tumor challenge using VEGFR1-1087, -770, -417 peptides conjugated with IFA (FIG. 6). Significant suppression of tumor growth was observed with the vaccination using VEGFR1-1087, -770 peptides conjugated with IFA. Furthermore, significant inhibitions of tumor growth were observed in various tumor cells (data not shown).

These results strongly suggest that the anti tumor effects induced with the vaccination using the peptides derived from VEGFR1 might be mediated by the inhibition of tumor-angiogenesis. Thus, vaccination with epitope peptides derived from VEGFR1 could affect the growth of the tumor cells through the effects on the VEGFR1-expressing endothelial cells of the vessels which support the tumor growth in vivo in this A2/Kb TGM-tumor system.

Discussion

Identification of the tumor associate antigens (TAAs) has enabled the clinical development of peptide-based cancer vaccine, which could induce CTLs and lyse tumor cells in HLA class I restricted fashion (Bruggen et al., (1991) Science. 254: 1643-7, Boon et al., (1996) J. Exp. Med. 183: 725-9, Rosenberg et al., (1998) Nat. Med. 4: 321-7, Butterfield et al., (1999) Cancer Res. 59: 3134-42). Until now, multiple clinical trials using TAA peptides have reported that tumor regressions were observed in approximately 20% rate of the melanoma patients. However, complete response has rarely been reported (Rosenberg et al., (1998) Nat. Med. 4: 321-7. Nestle et al., (1998) Nat. Med. 4: 328-32, Thurner et al., (1999) J. Exp. Med. 190: 1669-78, Belli et al., (2002) Parmiani. J. Clin. Oncol. 20: 4169-80, Coulie et al., (2002) Immunol. Rev. 188: 33-42). One of the possible reasons of modest clinical efficacy could be loss or down-regulation of HLA class I molecules on the tumor cells (Cormier et al., (1998) Int. J. Cancer. 75: 517-24, Paschen et al., (2003) Int. J. Cancer. 103: 759-67, Fonteneau et al., (1997). J. Immuol. 159: 2831-9, Reynolds et al., (1998) J. Immunol. 161: 6970-6). The frequency of tumors showing some alteration in expression of HLA class I molecules has been estimated to be more than 40% (Cormier et al., (1998) Int. J. Cancer. 75: 517-24, Paschen et al., (2003) Int. J. Cancer. 103: 759-67). Thus, significant portion of tumor cells could escape from the CTLs specific to the class I-epitope, even if CTLs could be successfully induced by cancer vaccine targeting tumor cells themselves. These problems can be overcome with the development of effective vaccine against tumor angiogenesis, since endothelial cells are genetically stable, do not show down-regulation of HLA Class I molecules, and are critically involved in the progression of a variety of tumors. Furthermore, the CTLs could directly cause damage to the endothelial cells without penetrating any other tissue, and lysis of even low numbers of endothelial cells within tumor vasculature will result in destruction of vessel integrity leading to inhibition of large numbers of tumor cells (Folkman, J. (1995) Nat. Med. 1: 27-31). Therefore, endothelial cells are a good target for cancer immunotherapy. To specifically and efficiently prevent tumor-angiogenesis with CTL response, the appropriated target needs to be selected among the molecules related to angiogenesis.

The results presented here, in vitro and in vivo, demonstrate that VEGFR1 can be used as target of immunological therapy using cellular immunity and support the definitive rationale of the clinical development of this strategy against a broad range of cancers.

INDUSTRIAL APPLICABILITY

The present invention provides novel peptides, which induce cytotoxic T cells by targeting endothelial cells formed in a wide range of tumor tissues, and are extremely effective as cancer vaccines. The present invention also provides immunogenic compositions comprising these peptides for treating and preventing tumors.

While the invention has been described in detail and with reference to specific embodiments thereof, it will be apparent to one skilled in the art that various changes and modifications can be made therein without departing from the spirit and scope of the invention.

The invention claimed is:

1. A method of treating angiogenesis-mediated disease in a subject comprising administering to the subject a composition comprising a peptide selected from the group consisting of:
   (a) an isolated peptide consisting of the amino acid sequence of SEQ ID NO: 2,
   (b) an isolated peptide having cytotoxic T cell inducibility, wherein the peptide consists of the amino acid sequence of SEQ ID NO: 2, in which 1 or 2 amino acids are substituted,
   and wherein the second amino acid from the N terminus is leucine or methionine, and the C-terminal amino acid is valine or leucine.

2. The method of claim 1, wherein the angiogenesis-mediated disease is selected from the group consisting of diabetic retinopathy, chronic rheumatoid arthritis, psoriasis, and atherosclerosis.

3. A method of inhibiting angiogenesis at a diseased site in a subject comprising administering to the subject a composition comprising a peptide selected from the group consisting of:
   (a) an isolated peptide consisting of the amino acid sequence of SEQ ID NO: 2,
   (b) an isolated peptide having cytotoxic T cell inducibility, wherein the peptide consists of the amino acid sequence of SEQ ID NO: 2, in which 1 or 2 amino acids are substituted,
   and wherein the second amino acid from the N terminus is leucine or methionine, and the C-terminal amino acid is valine or leucine, as the active ingredient.

4. The method of claim 3, wherein the subject expresses HLA-A02.

5. The method of claim 3, wherein the diseased site comprises a malignant tumor or metastasis of a malignant tumor.

6. The method of claim 3, wherein the diseased site comprises VEGFR1 expressing cells.

* * * * *

SEQUENCE LISTING

<160> NUMBER OF SEQ ID NOS: 45

<210> SEQ ID NO 1
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201 with high cytotoxic T lymphocyte (CTL)
      inducibility

<400> SEQUENCE: 1

Val Leu Leu Trp Glu Ile Phe Ser Leu
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201 with high cytotoxic T lymphocyte (CTL)

-continued inducibility

<400> SEQUENCE: 2

Thr Leu Phe Trp Leu Leu Leu Thr Leu
 1               5

<210> SEQ ID NO 3
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 3

Ile Leu Leu Ser Glu Asn Asn Val Val
 1               5

<210> SEQ ID NO 4
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 4

Cys Val Ala Ala Thr Leu Phe Trp Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 5

Ala Leu Met Thr Glu Leu Lys Ile Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 6

Lys Met Leu Lys Glu Gly Ala Thr Ala
 1               5

<210> SEQ ID NO 7
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 7

Leu Met Thr Glu Leu Lys Ile Leu Thr

<210> SEQ ID NO 8
<211> LENGTH: 9
<212> TYPE: PRT
<213> ORGANISM: Artificial Sequence
<220> FEATURE:
<223> OTHER INFORMATION: synthetic vascular endothelial growth factor receptor 1 (VEGFR1, Flt-1) epitope peptide binding HLA-A*0201

<400> SEQUENCE: 8

Ile Leu Thr His Ile Gly His His Leu
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic vascular endothelial growth factor receptor 1 (VEGFR1, Flt-1) epitope peptide binding HLA-A*0201

<400> SEQUENCE: 9

Asn Ile Leu Leu Ser Glu Asn Asn Val
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic vascular endothelial growth factor receptor 1 (VEGFR1, Flt-1) epitope peptide binding HLA-A*0201

<400> SEQUENCE: 10

Tyr Leu Thr His Arg Gln Thr Asn Thr
1               5

<210> SEQ ID NO 11
<211> LENGTH: 10
<212> TYPE: PRT
<213> ORGANISM: Artificial Sequence
<220> FEATURE:
<223> OTHER INFORMATION: synthetic vascular endothelial growth factor receptor 1 (VEGFR1, Flt-1) epitope peptide binding HLA-A*0201

<400> SEQUENCE: 11

Lys Leu Gly Asp Leu Leu Gln Ala Asn Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic vascular endothelial growth factor receptor 1 (VEGFR1, Flt-1) epitope peptide binding HLA-A*0201

<400> SEQUENCE: 12

Leu Leu Ser Glu Asn Asn Val Val Lys Ile
1               5                   10

<210> SEQ ID NO 13
<211> LENGTH: 10

-continued

```
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201 with high cytotoxic T lymphocyte (CTL)
      inducibility

<400> SEQUENCE: 13

Asn Leu Thr Ala Thr Leu Ile Val Asn Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 14

Ser Leu Gly Gly Ser Pro Tyr Pro Gly Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 15

Gln Met Asp Glu Asp Phe Cys Ser Arg Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 16

Gly Val Leu Leu Trp Glu Ile Phe Ser Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 17

Ile Ile Met Asp Pro Asp Glu Val Pro Leu
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic vascular endothelial growth factor
``` receptor 1 (VEGFR1, Flt-1) epitope peptide binding
HLA-A*0201

<400> SEQUENCE: 18

Phe Gln Val Ala Arg Gly Met Glu Phe Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 19

Tyr Leu Thr His Arg Gln Thr Asn Thr Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*0201

<400> SEQUENCE: 20

Ile Leu Leu Arg Thr Val Asn Asn Arg Thr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 21

Lys Tyr Gly Asn Leu Ser Asn Tyr Leu
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 22

Asn Tyr Leu Lys Ser Lys Arg Asp Leu
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 23

Glu Tyr Lys Ala Leu Met Thr Glu Leu
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 24

Arg Tyr Val Asn Ala Phe Lys Phe Met
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 25

Ser Tyr Gly Val Leu Leu Trp Glu Ile
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 26

Arg Phe Ala Glu Leu Val Glu Lys Leu
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 27

Glu Phe Ala Arg Glu Arg Leu Lys Leu
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 28

Lys Ser Asn Leu Glu Leu Ile Thr Leu
1               5

<210> SEQ ID NO 29

```
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 29

Lys Trp Glu Phe Ala Arg Glu Arg Leu
 1               5

<210> SEQ ID NO 30
<211> LENGTH: 9
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 30

Pro Tyr Asp Ala Ser Lys Trp Glu Phe
 1               5

<210> SEQ ID NO 31
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 31

Asn Tyr Leu Lys Ser Lys Arg Asp Leu Phe
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402 with high cytotoxic T lymphocyte (CTL)
      inducibility

<400> SEQUENCE: 32

Ser Tyr Gly Val Leu Leu Trp Glu Ile Phe
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 33

Ser Tyr Ser Phe Gln Val Ala Arg Gly Met
 1               5                  10

<210> SEQ ID NO 34
<211> LENGTH: 10
<212> TYPE: PRT
<213> ORGANISM: Artificial Sequence
<220> FEATURE:
```

```
<223> OTHER INFORMATION: synthetic vascular endothelial growth factor
      receptor 1 (VEGFR1, Flt-1) epitope peptide binding
      HLA-A*2402

<400> SEQUENCE: 34

Lys Ile Leu Thr His Ile Gly His His Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 35

Ser Phe Gln Val Ala Arg Gly Met Glu Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 36

Arg Tyr Val Asn Ala Phe Lys Phe Met Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 37

Lys Ile Gln Gln Glu Pro Gly Ile Ile Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 38

Lys Ala Leu Met Thr Glu Leu Lys Ile Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 39
```

```
Glu Leu Val Glu Lys Leu Gly Asp Leu Leu
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: synthetic vascular endothelial growth factor
      receptor 1 (VEGFR1, Flt-1) epitope peptide binding
      HLA-A*2402

<400> SEQUENCE: 40

Lys Ser Asp Val Trp Ser Tyr Gly Val Leu
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: synthetic CEA peptide positive control

<400> SEQUENCE: 41

Asp Val Leu Tyr Gly Pro Asp Thr Pro Ile
 1               5                  10

<210> SEQ ID NO 42
<211> LENGTH: 9
<212> TYPE: PRT
<213> ORGANISM: Artificial Sequence
<220> FEATURE:
<223> OTHER INFORMATION: synthetic CMV peptide A02 positive control

<400> SEQUENCE: 42

Asn Leu Val Pro Met Val Ala Thr Val
 1               5

<210> SEQ ID NO 43
<211> LENGTH: 9
<212> TYPE: PRT
<213> ORGANISM: Artificial Sequence
<220> FEATURE:
<223> OTHER INFORMATION: synthetic CMV peptide A24 positive control

<400> SEQUENCE: 43

Gln Tyr Asp Pro Val Ala Ala Leu Phe
 1               5

<210> SEQ ID NO 44
<211> LENGTH: 5777
<212> TYPE: DNA
<213> ORGANISM: Homo sapiens
<220> FEATURE:
<223> OTHER INFORMATION: vascular endothelial growth factor receptor 1
      (VEGFR1, Flt-1)
<220> FEATURE:
<221> NAME/KEY: CDS
<222> LOCATION: (250)..(4266)
<223> OTHER INFORMATION: VEGFR1

<400> SEQUENCE: 44
gcggacactc ctctcggctc ctccccggca gcggcggcgg ctcggagcgg gctccggggc      60
tcgggtgcag cggccagcgg gcctggcggc gaggattacc cggggaagtg gttgtctcct    120
ggctggagcc gcgagacggg cgctcagggc gcggggccgg cggcggcgaa cgagaggacg    180
gactctggcg gccgggtcgt tggccggggg agcgcgggca ccgggcgagc aggccgcgtc    240
```

```
gcgctcacca tggtcagcta ctgggacacc ggggtcctgc tgtgcgcgct gctcagctgt    300
ctgcttctca caggatctag ttcaggttca aaattaaaag atcctgaact gagtttaaaa    360
ggcacccagc acatcatgca agcaggccag acactgcatc tccaatgcag ggggaagca     420 gcccataaat ggtctttgcc tgaaatggtg agtaaggaaa gcgaaaggct gagcataact    480
aaatctgcct gtggaagaaa tggcaaacaa ttctgcagta ctttaacctt gaacacagct    540
caagcaaacc acactggctt ctacagctgc aaatatctag ctgtacctac ttcaaagaag    600
aaggaaacag aatctgcaat ctatatattt attagtgata caggtagacc tttcgtagag    660
atgtacagtg aaatccccga aattatacac atgactgaag aagggagct cgtcattccc     720 tgccgggtta cgtcacctaa catcactgtt actttaaaaa agtttccact tgacactttg    780
atccctgatg gaaaacgcat aatctgggac agtagaaagg gcttcatcat atcaaatgca    840
acgtacaaag aaatagggct tctgacctgt gaagcaacag tcaatgggca tttgtataag    900
acaaactatc tcacacatcg acaaaccaat acaatcatag atgtccaaat aagcacacca    960
cgcccagtca aattacttag aggccatact cttgtcctca attgtactgc taccactccc   1020
ttgaacacga gagttcaaat gacctggagt taccctgatg aaaaaaataa gagagcttcc   1080
gtaaggcgac gaattgacca aagcaattcc catgccaaca tattctacag tgttcttact   1140
attgacaaaa tgcagaacaa agacaaagga ctttatactt gtcgtgtaag gagtggacca   1200
tcattcaaat ctgttaacac ctcagtgcat atatatgata aagcattcat cactgtgaaa   1260
catcgaaaac agcaggtgct tgaaaccgta gctggcaagc ggtcttaccg gctctctatg   1320
aaagtgaagg catttccctc gccggaagtt gtatggttaa agatgggtt  acctgcgact   1380 gagaaatctg ctcgctattt gactcgtggc tactcgttaa ttatcaagga cgtaactgaa   1440
gaggatgcag ggaattatac aatcttgctg agcataaaac agtcaaatgt gtttaaaaac   1500
ctcactgcca ctctaattgt caatgtgaaa ccccagattt acgaaaaggc cgtgtcatcg   1560
tttccagacc cggctctcta cccactgggc agcagacaaa tcctgacttg taccgcatat   1620
ggtatccctc aacctacaat caagtggttc tggcaccccct gtaaccataa tcattccgaa   1680
gcaaggtgtg acttttgttc aataatgaa gagtcccttta tcctggatgc tgacagcaac   1740
atgggaaaca gaattgagag catcactcag cgcatggcaa aatagaaggg aaagaataag   1800
atggctagca ccttggttgt ggctgactct agaatttctg gaatctacat ttgcatagct   1860
tccaataaag ttgggactgt gggaagaaac ataagctttt atatcacaga tgtgccaaat   1920
gggtttcatg ttaacttgga aaaaatgccg acggaaggag aggacctgaa actgtcttgc   1980
acagttaaca agttcttata cagagacgtt acttggattt tactgcggac agttaataac   2040
agaacaatgc actacagtat tagcaagcaa aaaatggcca tcactaagga gcactccatc   2100
actcttaatc ttaccatcat gaatgttttcc ctgcaagatt caggcaccta tgcctgcaga   2160
gccaggaatg tatacacagg ggaagaaatc ctccagaaga aagaaattac aatcagagat   2220
caggaagcac catacctcct gcgaaacctc agtgatcaca cagtggccat cagcagttcc   2280
accactttag actgtcatgc taatggtgtc cccgagcctc agatcacttg gtttaaaaac   2340
aaccacaaaa tacaacaaga gcctggaatt attttaggac caggaagcag cacgctgttt   2400
attgaaagag tcacagaaga ggatgaaggt gtctatcact gcaaagccac caaccagaag   2460
ggctctgtgg aaagttcagc atacctcact gttcaaggaa cctcggacaa gtctaatctg   2520
gagctgatca ctctaacatg cacctgtgtg gctgcgactc tcttctggct cctattaacc   2580
ctccttatcc gaaaaatgaa aaggtcttct tctgaaataa agactgacta cctatcaatt   2640
```

```
ataatggacc cagatgaagt tcctttggat gagcagtgtg agcggctccc ttatgatgcc    2700
agcaagtggg agtttgcccg ggagagactt aaactgggca atcacttgg aagaggggct    2760 tttggaaaag tggttcaagc atcagcattt ggcattaaga aatcacctac gtgccggact    2820
gtggctgtga aaatgctgaa agaggggcc acggccagcg agtacaaagc tctgatgact    2880
gagctaaaaa tcttgaccca cattggccac catctgaacg tggttaacct gctgggagcc    2940
tgcaccaagc aaggagggcc tctgatggtg attgttgaat actgcaaata tggaaatctc    3000
tccaactacc tcaagagcaa acgtgactta ttttttctca acaaggatgc agcactacac    3060
atggagccta agaaagaaaa aatggagcca ggcctggaac aaggcaagaa accaagacta    3120
gatagcgtca ccagcagcga aagctttgcg agctccggct tcaggaaga taaaagtctg    3180 agtgatgttg aggaagagga ggattctgac ggtttctaca aggagcccat cactatggaa    3240
gatctgattt cttacagttt tcaagtggcc agaggcatgg agttcctgtc ttccagaaag    3300
tgcattcatc gggacctggc agcgagaaac attctttat ctgagaacaa cgtggtgaag    3360
atttgtgatt ttggccttgc ccgggatatt tataagaacc ccgattatgt gagaaaagga    3420
gatactcgac ttcctctgaa atggatggct cccgaatcta tctttgacaa aatctacagc    3480
accaagagcg acgtgtggtc ttacggagta ttgctgtggg aaatcttctc cttaggtggg    3540
tctccatacc caggagtaca aatggatgag acttttgca gtcgcctgag ggaaggcatg    3600
aggatgagag ctcctgagta ctctactcct gaaatctatc agatcatgct ggactgctgg    3660
cacagagacc caaaagaaag gccaagattt gcagaacttg tggaaaaact aggtgatttg    3720
cttcaagcaa atgtacaaca ggatggtaaa gactacatcc caatcaatgc catactgaca    3780
ggaaatagtg ggtttacata ctcaactcct gccttctctg aggacttctt caaggaaagt    3840
atttcagctc cgaagtttaa ttcaggaagc tctgatgatg tcagatatgt aaatgctttc    3900
aagttcatga gcctggaaag aatcaaaacc tttgaagaac ttttaccgaa tgccacctcc    3960
atgtttgatg actaccaggg cgacagcagc actctgttgg cctctcccat gctgaagcgc    4020
ttcacctgga ctgacagcaa acccaaggcc tcgctcaaga ttgacttgag agtaaccagt    4080
aaaagtaagg agtcggggct gtctgatgtc agcaggccca gtttctgcca ttccagctgt    4140
gggcacgtca gcgaaggcaa gcgcaggttc acctacgacc acgctgagct ggaaaggaa    4200 atcgcgtgct gctccccgcc cccagactac aactcggtgg tcctgtactc caccccaccc    4260
atctagagtt tgacacgaag ccttatttct agaagcacat gtgtatttat accccaggaa    4320
aactagcttt tgccagtatt atgcatatat aagtttacac ctttatcttt ccatgggagc    4380
cagctgcttt ttgtgatttt tttaatagtg ctttttttt ttgactaaca agaatgtaac    4440
tccagataga gaaatagtga caagtgaaga acactactgc taaatcctca tgttactcag    4500
tgttagagaa atccttccta aacccaatga cttccctgct ccaaccccg ccacctcagg    4560 gcacgcagga ccagtttgat tgaggagctg cactgatcac ccaatgcatc acgtacccca    4620
ctgggccagc cctgcagccc aaaacccagg caacaagcc cgttagcccc aggggatcac    4680
tggctggcct gagcaacatc tcgggagtcc tctagcaggc ctaagacatg tgaggaggaa    4740
aggaaaaaaa agcaaaaagc aagggagaaa agagaaaccg ggagaaggca tgagaaagaa    4800
tttgagacgc accatgtggg cacggagggg gacgggctc agcaatgcca tttcagtggc    4860
ttcccagctc tgacccttct acatttgagg gcccagccag gagcagatgg acagcgatga    4920
ggggacattt tctggattct gggaggcaag aaaaggacaa atatctttt tggaactaaa    4980 gcaaatttta gacctttacc tatggaagtg gttctatgtc cattctcatt cgtggcatgt    5040
```

```
tttgatttgt agcactgagg gtggcactca actctgagcc catactttg gctcctctag    5100 taagatgcac tgaaaactta gccagagtta ggttgtctcc aggccatgat ggccttacac    5160
tgaaaatgtc acattctatt ttgggtatta atatatagtc cagacactta actcaatttc    5220
ttggtattat tctgttttgc acagttagtt gtgaaagaaa gctgagaaga atgaaaatgc    5280
agtcctgagg agagttttct ccatatcaaa cgagggctg atggaggaaa aaggtcaata    5340
aggtcaaggg aagaccccgt ctctatacca accaaaccaa ttcaccaaca cagttgggac    5400
ccaaaacaca ggaagtcagt cacgtttcct tttcatttaa tggggattcc actatctcac    5460
actaatctga aaggatgtgg aagagcatta gctggcgcat attaagcact ttaagctcct    5520
tgagtaaaaa ggtggtatgt aatttatgca aggtatttct ccagttggga ctcaggatat    5580
tagttaatga gccatcacta gaagaaaagc ccattttcaa ctgctttgaa acttgcctgg    5640
ggtctgagca tgatgggaat agggagacag ggtaggaaag ggcgcctact cttcagggtc    5700
taaagatcaa gtgggccttg gatcgctaag ctggctctgt tgatgctat ttatgcaagt    5760 tagggtctat gtattta                                                    5777
```

<210> SEQ ID NO 45
<211> LENGTH: 1338
<212> TYPE: PRT
<213> ORGANISM: Homo sapiens
<220> FEATURE:
<223> OTHER INFORMATION: vascular endothelial growth factor receptor 1
      (VEGFR1, Flt-1)

<400> SEQUENCE: 45

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220
```

-continued

```
Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
            245                 250                 255

Pro Leu Asn Thr Arg Val Gln Met Thr Trp Ser Tyr Pro Asp Glu Lys
        260                 265                 270

Asn Lys Arg Ala Ser Val Arg Arg Ile Asp Gln Ser Asn Ser His
    275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
            325                 330                 335

Lys His Arg Lys Gln Gln Val Leu Glu Thr Val Ala Gly Lys Arg Ser
        340                 345                 350

Tyr Arg Leu Ser Met Lys Val Lys Ala Phe Pro Ser Pro Glu Val Val
    355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
        420                 425                 430

Lys Ala Val Ser Ser Phe Pro Asp Pro Ala Leu Tyr Pro Leu Gly Ser
    435                 440                 445

Arg Gln Ile Leu Thr Cys Thr Ala Tyr Gly Ile Pro Gln Pro Thr Ile
450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
        500                 505                 510

Glu Gly Lys Asn Lys Met Ala Ser Thr Leu Val Val Ala Asp Ser Arg
    515                 520                 525

Ile Ser Gly Ile Tyr Ile Cys Ile Ala Ser Asn Lys Val Gly Thr Val
530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
        580                 585                 590

Arg Thr Val Asn Asn Arg Thr Met His Tyr Ser Ile Ser Lys Gln Lys
    595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655
```

```
Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
                755                 760                 765

Ala Thr Leu Phe Trp Leu Leu Leu Thr Leu Leu Ile Arg Lys Met Lys
        770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
        930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
                980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
```

-continued

```
         1075                1080                1085
Leu Trp Glu Ile Phe Ser Leu Gly Gly Ser Pro Tyr Pro Gly Val Gln
    1090                1095                1100

Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
                1125                1130                1135

Trp His Arg Asp Pro Lys Glu Arg Pro Arg Phe Ala Glu Leu Val Glu
                1140                1145                1150

Lys Leu Gly Asp Leu Leu Gln Ala Asn Val Gln Gln Asp Gly Lys Asp
            1155                1160                1165

Tyr Ile Pro Ile Asn Ala Ile Leu Thr Gly Asn Ser Gly Phe Thr Tyr
        1170                1175                1180

Ser Thr Pro Ala Phe Ser Glu Asp Phe Phe Lys Glu Ser Ile Ser Ala
1185                1190                1195                1200

Pro Lys Phe Asn Ser Gly Ser Ser Asp Asp Val Arg Tyr Val Asn Ala
                1205                1210                1215

Phe Lys Phe Met Ser Leu Glu Arg Ile Lys Thr Phe Glu Glu Leu Leu
                1220                1225                1230

Pro Asn Ala Thr Ser Met Phe Asp Asp Tyr Gln Gly Asp Ser Ser Thr
            1235                1240                1245

Leu Leu Ala Ser Pro Met Leu Lys Arg Phe Thr Trp Thr Asp Ser Lys
        1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
                1285                1290                1295

Cys Gly His Val Ser Glu Gly Lys Arg Arg Phe Thr Tyr Asp His Ala
            1300                1305                1310

Glu Leu Glu Arg Lys Ile Ala Cys Cys Ser Pro Pro Asp Tyr Asn
        1315                1320                1325

Ser Val Val Leu Tyr Ser Thr Pro Pro Ile
    1330                1335
```